US006974791B2

(12) United States Patent
Wong et al.

(10) Patent No.: US 6,974,791 B2
(45) Date of Patent: Dec. 13, 2005

(54) ENDOTHELIAL SPECIFIC TARGETING

(75) Inventors: Michael K. Wong, Wexford, PA (US); Ruth A. Modzelewski, Glenshaw, PA (US); Charles Komen Brown, Chicago, IL (US); Candace S. Johnson, Pittsburgh, PA (US); Donald L. Trump, Pittsburgh, PA (US)

(73) Assignee: The University of Pittsburgh, Pittsburgh, PA (US)

( * ) Notice: Subject to any disclaimer, the term of this patent is extended or adjusted under 35 U.S.C. 154(b) by 600 days.

(21) Appl. No.: 09/810,700

(22) Filed: Mar. 16, 2001

(65) Prior Publication Data

US 2002/0058615 A1 May 16, 2002

Related U.S. Application Data

(60) Provisional application No. 60/189,793, filed on Mar. 16, 2000.

(51) Int. Cl.[7] ........................ A61K 38/00; A61K 38/08; C07K 7/00
(52) U.S. Cl. .............................. 514/2; 514/15; 530/328
(58) Field of Search ....................... 514/2, 15; 530/328, 530/300

(56) References Cited

U.S. PATENT DOCUMENTS

| 5,855,866 A | | 1/1999 | Thorpe et al. ............. 424/1.49 |
| 5,965,132 A | * | 10/1999 | Thorpe et al. |
| 6,022,541 A | * | 2/2000 | Senger et al. ............ 424/172.1 |
| 6,051,230 A | | 4/2000 | Thorpe et al. |
| 6,261,535 B1 | | 7/2001 | Thorpe et al. ............. 424/1.49 |
| 6,348,350 B1 | * | 2/2002 | Goddrd et al. |
| 6,350,450 B1 | * | 2/2002 | Godowski et al. |

FOREIGN PATENT DOCUMENTS

| WO | WO 90/03801 | * | 4/1990 |
| WO | WO 00/04052 | * | 1/2000 |
| WO | WO 00/23476 | * | 1/2000 |
| WO | WO 01/62930 A1 | | 8/2001 |

OTHER PUBLICATIONS

Abstract of Peters et al (British journal of Cancer, 1998, vol. 77, pp. 51–56).*
Alberts et al (Molecular Biology of the Cell, 1989, pp. 962–963.*
Accession No. AAM49503, 1998.*
Accession No. AAU77264, 1998.*
Accession No. AAO20102, 1999.*
Accession No. AAO14302, 1999.*
Accession No. AAU78102, 1999.*
Accession No. AAE19825, 2002.*
Accession No. AAE20195, 2002.*
Ellerby, H. M. et al.; Anti-Cancer Activity of Targeted Pro–Apoptotic Peptides; Nature Medicine, vol. 5, No. 9, pp. 1032–1038; 1999.

Ghose et al., Preparation of antibody–linked cytotoxic agents. Methods Enzymol. 93: 280–333, 1983.
Ghose et al., The design of cytotoxic–agent–antibody conjugates. Crit. Rev. Ther. Drug. Carrier Syst. 3(4):263–359. 1987.
Pierschbacher M.D. and Ruoslahti E. The cell attachment activity of fibronectin can be duplicated by small fragments of the molecule. Nature 1984; 309:30.
Koivunen E, Gay D, Ruoslahti E. Selection of peptides binding to the $\alpha_5\beta_1$ integrin from phage display library. J Biol Chem 1993; 268: 20205.
Koivunen E, Wang B, Ruoslahti E. Isolation of a highly specific ligand for the $\alpha_5\beta_1$ integrin from a phage display library. J Cell Biol 1994; 124:373.
Healy JM, Murayama O, Maeda T, et al. Peptide ligands for integrin $\alpha_5\beta_3$ selected from random phage display libraries. Biochemistry 1995; 34:3948.
Pasqualini R, Ruoslahti, E. Organ targeting in vivo using phage display peptide libraries. Nature 1996; 380:364.
Rajotte D, Arap W, Hagedorn M, et al. Molecular heterogeneity of the vascular endothelium revealed by in vivo phage display. J Clin Invest 1998; 102:430.
Pasqualini R, Koivunen E, Kain R, et al. Aminopeptidase N is a receptor for tumor–homing peptides and a target for inhibiting angiogenesis. Ca Res 2000; 60:722.
Smith GP. Filamentous fusion phage: novel expression vectors that display cloned antigens on the virion surface. Science 1985; 228:1315.
Scott JK, Smith GP. Searching for peptide ligands with an epitope library. Science 1990; 249:386.
Clackson T, Wells JA. In vitro selection from protein and peptide libraries. Trends Biothechnol 1994; 12:173.
Colas P, Cohen B, Jessen T, et al. Genetic selection of peptide aptamers that recognize and inhibit cyclin–dependent kinase 2. Nature 1996; 380:548.
Lu Z, Murray KS, van Cleave V, et al. Expression of thioredoxin random peptide libraries on *Escherichia coli* (*E. coli*) cell surface as functional fusions to flagellin: a system designed for exploring protein–protein interactions. Bio/Technology (NU) 1995; 13:366.

(Continued)

*Primary Examiner*—Karen A. Canella
(74) *Attorney, Agent, or Firm*—Reed Smith LLP

(57) ABSTRACT

Peptide motifs which define specificity of tumor-derived endothelial cells. These peptides possess a charge motif of positive-positive-hydrophobic which is important in determining the specificity of binding to tumor-derived endothelium. The specific molecular peptide motifs will facilitate diverse therapeutic and diagnostic applications including: anti-angiogenic therapies to be used in alone or in conjunction with standard therapies; imaging tools for both detection of very small metastasis that are undetectable by current techniques; for monitoring tumor response; for targeting and directing chemotherapy drugs to the tumor; for treatment of chronic inflammatory diseases such as rheumatoid arthritis and psoriasis, for treating some forms of blindness; as well as other diagnostic and therapeutic applications.

13 Claims, 9 Drawing Sheets

OTHER PUBLICATIONS

Baatout S. Endothelial differentiation using Matrigel (*Review*). Anticancer Res 1997; 17:451.

Zhu D, Pauli BU. Generation of monoclonal antibodies directed against organ–specific endothelial cell surface determinants. J Histochem Cytochem 1991; 39:1137.

Pierschbacher MD, Ruoslahti E. Variants of the cell recognition site of fibronectin that retain attachment–promoting activity. Proc Natl Acad Sci USA 1984; 81:5985.

Yamada KM, Kennedy DW. Dualistic nature of adhesive protein function: fibronectin and its biologically active peptide fragments can autoinhibit fibronectin function. J Cell Biol 1984; 99:29.

Gartner TK, Bennett JS. The tetrapeptide analog of the cell attachment site of fibronectin inhibits platelet aggregation and fibrinogen binding to activated platelets. J Biol Chem 1985; 260:11891.

Plow EF, Pierschbacher MD, Ruoslahti E, et al. The effect of Arg–Gly–Asp containing peptides on fibrinogen and von Willebrand factor binding to platelets. Proc Natl Acad Sci USA 1985; 82:8057.

Brown CK, Modzelewski RA, Johnson CS, and Wong MKK. A novel approach for the identification of unique tumor vasculature binding peptides using an *E. coli* peptide display library. Ann. Of Surg. Onc. 2000; 7(10): 743–749.

Suzuki S, Oldberg A, Hayman EG, et al. Complete amino acid sequence of human vitronectin deduced from cDNA. Similarity of cell attachment sites in vitronectin and fibronectin. EMBO J 1985; 4:2519.

Gardner JM, Hynes RO. Interaction of fibronectin with its receptor on platelets. Cell 1985; 42:439.

Ito Y, Iwamoto Y, Tanaka K, et al. A quantitative assay using basement membrane extracts to study tumor angiogenesis in vivo. Int J Cancer 1996; 67:148.

Modzelewski RA, Davies P, Watkins SC, Auerback R, Chang M–J, Johnson CS. Isolation and identification of fresh tumor–derived endothelial cells from a murine RIF–1 fibrosarcoma. Ca Res 1994, 54:336–339.

\* cited by examiner

| | | | | |
|---|---|---|---|---|
| ARG-ARG-VAL-LEU | 2 | | | |
| ARG-ARG-HIS-GLU | 2 | | | |
| ARG-ARG-SER | 3 | | | |
| ARG-ARG- | 2 | | | |
| ARG-HIS- | 2 | SIZE # | 3-MER | 4-MER |
| GLY-ARG-HIS- | 2 | | | |
| GLY-ARG-HIS | 3 | | | |
| ARG-LYS- | 2 | | | |
| ARG-LYS- | 2 | 2X | 9 | 4 |
| HIS-LYS- | 2 | | | |
| LYS-ARG-ALA | 3 | | | |
| SER-LYS-ARG- | 2 | 3X | 4 | 0 |
| ARG-SER-ARG | 3 | | | |
| ARG-SER- | 2 | | | |
| SER-ARG-ALA | 2 | | | |
| SER-ARG-GLY | 2 | | | |
| ARG-GLY- | 2 | | | |

FIG. 4

SEQUENCE LISTING

```
<160> NUMBER OF SEQ ID NOS: 8

<210> SEQ ID NO 1
<211> LENGTH: 9
<212> TYPE: PRT
<213> ORGANISM: mammalian
```

```
<400> SEQUENCE: 1

Cys Gly Gly Arg His Ser Gly Gly Cys
1               5

<210> SEQ ID NO 2
<211> LENGTH: 9
<212> TYPE: PRT
<213> ORGANISM: mammalian

<400> SEQUENCE: 2

Cys Gly Gly Arg Lys Leu Gly Gly Cys
1               5

<210> SEQ ID NO 3
<211> LENGTH: 9
<212> TYPE: PRT
<213> ORGANISM: mammalian

<400> SEQUENCE: 3

Cys Gly Gly Arg Arg Leu Gly Gly Cys
1               5

<210> SEQ ID NO 4
<211> LENGTH: 10
<212> TYPE: PRT
<213> ORGANISM: mammalian

<400> SEQUENCE: 4

Cys Gly Gly Arg Arg Ser Arg Gly Gly Cys
1               5                   10

<210> SEQ ID NO 5
<211> LENGTH: 10
<212> TYPE: PRT
<213> ORGANISM: mammalian

<400> SEQUENCE: 5

Cys Leu Leu Arg Arg Ser Arg Leu Leu Cys
1               5                   10

<210> SEQ ID NO 6
<211> LENGTH: 4
<212> TYPE: PRT
<213> ORGANISM: mammalian

<400> SEQUENCE: 6

Cys Gly Pro Cys
1

<210> SEQ ID NO 7
<211> LENGTH: 9
<212> TYPE: PRT
<213> ORGANISM: mammalian

<400> SEQUENCE: 7

Cys Glu Leu Arg Gly Asp Gly Trp Cys
1               5

<210> SEQ ID NO 8
<211> LENGTH: 9
<212> TYPE: PRT
<213> ORGANISM: mammalian
```

```
<400> SEQUENCE: 8

Cys Gly Gly Gly Gly Gly Gly Cys
1               5
```

ENDOTHELIAL SPECIFIC TARGETING

This non-provisional application claims the benefit under 35 U.S.C. 119(e) of U.S. provisional application 60/189,793 filed Mar. 16, 2000.

FIELD OF THE INVENTION

The present invention relates generally to small peptide motifs which critically determine molecular specificity and possibly function relating to molecular targets of the tumor endothelium.

BACKGROUND OF THE INVENTION

Vascular endothelial cells cover the entire inner surface of blood vessels in the body. They play an important role in tissue homeostasis, fibrinolysis and coagulation, blood-tissue exchange, vascularization of normal and neoplastic tissues, and blood cell activation and migration during physiological and pathological processes. A unique aspect of endothelial cells is that although they present many common functional and morphological features, they also display remarkable heterogeneity in different organs. It has been shown that bovine aortic endothelial cells, when co-cultured with cells or matrix proteins from various organs, will change their phenotype to reflect their interaction with that particular tissue type. These phenotypes are, in part, mediated by molecular markers, which are expressed by these endothelial cells specific for the unique interaction. Based on the unique histologic appearance of tumor vasculature, it is postulated that expression of specific molecular endothelial markers probably also exist for the tumor-endothelial interaction. The ability to target these molecules would, in effect, specifically target the tumor endothelium, and hence, the tumor. Previous attempts to identify and target these specific molecular endothelial molecules have failed.

The importance of pathologic angiogenesis is well established in the clinical setting of cancer. Solid tumors are unable to grow much larger than 2 mm in diameter without a blood supply, and in order to express a malignant phenotype, tumors must induce new vessel growth. Tumors recruit endothelial cells during the process of angiogenesis. The recruited endothelial cells differentiate and express unique molecular markers specific for their association with tumor cells. The ability to identify and target these molecular markers would allow for specific targeting of the tumor vasculature as well as the tumor itself. Currently, there are no viable directed therapies targeting the endothelial cells and therapies are needed to provide novel and specific treatment alternatives.

Until recently, identification of tissue-specific endothelial markers has progressed slowly, partly because of difficulties in isolating pure populations of endothelial cells from tissues. A powerful technique utilizing phage display peptide libraries has been developed that allows for the selection of peptide sequences with desired binding specificities. In this system, peptides with as many as 109 permutations are expressed on the phage surface by fusion with a phage surface protein. The desired peptides are selected on the basis of binding to the target molecule. The strength of this technology is its ability to identify interactive proteins and other molecules without pre-existing notions about the nature of the interaction.

Using this methodology, various peptides with binding specificity to angiogenic endothelium and endothelial cells from various organs have been identified. These peptide sequences are typically three amino acids in length and the best characterized of these sequences is represented by the RGD (Arg-Gly-Asp) motif. This sequence was originally discovered in fibronectin, and later re-identified using in vivo phage peptide display library animal experiments. RGD is the cell attachment site for many other adhesive proteins.

The finding that only 3 amino acids would form an essential recognition site for cells in a very large protein was initially received with some skepticism. However, the observation was soon confirmed with regard to fibronectin and then extended to other proteins. Since then, other peptide motifs that identify and bind to specific targets on the endothelial cells of angiogenic vessels, brain, lungs, retina, and kidneys have been reported (Table 1). Also, the functional specificity of the 3-amino acid motif, NGR (Arg-Gly-Asp), has recently been described for angiogenic endothelium. It is important to point out that the reported motifs with binding to tumor endothelium are, in fact, specific for angiogenic endothelial cells and not specific for tumor-derived endothelium.

TABLE 1

Reported Peptide Motifs and Targeted Tissue

| Peptide Motifs | Tissue Target |
| --- | --- |
| RDG | Angiogenic Endothelium |
| NGR | Angiogenic Endothelium |
| GSL | Angiogenic Endothelium |
| GFE | Lung |
| RDV | Retina |
| SRL | Brain |

SUMMARY OF THE INVENTION

Embodiments of the present invention include purified peptide fragments with selective binding to tumor-derived endothelial cell, wherein the peptide fragment possesses a charge motif of positive-positive-neutral hydrophobic (++O). In a preferred embodiment, these purified peptide fragments have an amino acid length of between 2 and 50 residues.

A further embodiment of the invention includes the purified peptide fragments described above wherein the peptide fragment is operatively attached to a therapeutic agent capable of exerting a cytotoxic effect on tumor vasculature. Furthermore, this peptide fragment operatively attached to a therapeutic agent may exert a cytotoxic effect on tumor vasculature sufficient to lead to tumor necrosis. Additionally, these peptide fragments may be formulated as a pharmaceutical composition.

In further embodiments, purified peptide fragments of the present invention are linked to a diagnostic agent that is detectable upon imaging, such diagnostic agents include: paramagnetic, radioactive or fluorogenic ion. Specifically, the diagnostic agents utilized in embodiments of the invention include: chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III), erbium (III), iodine$^{123}$, technetium$^{99m}$, indium$^{111}$, rhenium$^{188}$, rhenium$^{186}$, copper$^{67}$, iodine$^{131}$, yttrium$^{90}$, iodine$^{125}$, astatine$^{211}$, and gallium$^{67}$.

Additional embodiments of the present invention include compositions useful for targeting tumor-derived endothelial cells, the composition being comprised of a peptide selected from the group consisting of SEQ ID NO:1 (Cys-Gly-Gly- Arg-His-Ser-Gly-Gly-Cys), SEQ ID NO: 2 (Cys-Gly-Gly-Arg-Lys-Leu-Gly-Gly-Cys), SEQ ID NO:3 (Cys-Gly-Gly-Arg-Arg-Leu-Gly-Gly-Cys), SEQ ID NO: 4 (Cys-Gly-Gly-Arg-Arg-Ser-Arg-Gly-Gly-Cys) and SEQ ID NO:5(Cys-Leu-Leu-Arg-Arg-Ser-Arg-Leu-Leu-Cys). In additional embodiments of the present invention, the compositions described above may include a peptide capable of being operatively attached or operatively attached to a therapeutic agent that is capable of exerting a cytotoxic effect on tumor vasculature, which in some instances may be sufficient to lead to tumor necrosis. Additionally, in additional embodiments of the invention these compositions may be formulated as a pharmaceutical composition.

In a further embodiment, the composition of the present invention described above is attached to a therapeutic agent which includes at least one of the following anticellular agents: a steroid, an antimetabolite, an anthracycline, a vinca alkaloid, an antibiotic, an alkylating agent, an epipodophyllotoxin, a plant-, fungus- or bacteria-derived toxin. Similarly, embodiments of the invention include composition of the present invention described above is attached to a therapeutic agent which includes at least one of the following cytotoxic agents: an A chain toxin, a ribosome inactivating protein, gelonin, .alpha.-sarcin, aspergillin, restrictocin, a ribonuclease, diphthia toxin, *Pseudomonas* exotoxin, a bacterial endotoxin, or the lipid A moiety of a bacterial endotoxin.

In additional embodiments, compositions of the present invention include peptides which are linked to a diagnostic agent that is detectable upon imaging, such diagnostic agents include: paramagnetic, radioactive or fluorogenic ion. Specifically, the diagnostic agents utilized in embodiments of the invention include: chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III),erbium (III), iodine$^{123}$, technetium$^{99m}$, indium$^{111}$, rhenium$^{188}$, rhenium$^{186}$, copper$^{67}$, iodine$^{131}$, yttrium$^{90}$, iodine$^{125}$, astatine$^{211}$, and gallium$^{67}$.

A further embodiment of the present invention includes a method for treating a diseased state in a mammal wherein the following is administered: an effective amount of a peptide fragment with selective binding to tumor-derived endothelial cells, wherein the peptide fragment possess the charge motif of positive-positive-neutral hydrophobic (++O). The diseased state may include chronic inflammatory diseases.

Embodiments of the present invention include peptide motifs/targeting peptides that define specificity of tumor-derived endothelial cells.

Embodiments of the present invention will facilitate anti-angiogenic therapies to be used either alone or in conjunction with standard anti-angiogenic therapies.

Furthermore, embodiments of the present invention include methods for use in diagnostic imaging tools for the detection of very small metastasis, as well as for monitoring tumor response to treatments.

An additional embodiment of the present invention encompasses targeting and directing chemotherapy drugs to the tumor.

Still further embodiments of the invention include treatments for chronic inflammatory diseases such as rheumatoid arthritis and psoriasis, as well as for some forms of blindness.

The present invention and its preferred embodiments will be better understood by way of reference to the detailed disclosure and to the accompanying drawings described hereinbelow.

BRIEF DESCRIPTION OF THE DRAWINGS

FIG. 4. A chart identifying the test peptide sequences with targeting sequences highlighted along with the frequency of the repeated peptides;

DETAILED DESCRIPTION OF THE PRESENT INVENTION

The present invention includes a system that can be used to identify specific molecular targets of the tumor endothelium. Given that small peptide motifs are able to critically determine molecular specificity and therefore function, a need was recognized in connection with identifying small peptide sequences or fragments, preferably less than 50 amino acids in length, that could define specificity of TDEC. An additional need included the determination of whether the physical characteristics of charge conformation of these motifs is important for the specificity.

The following rationale formed the basis of the identification of the molecular motifs in accordance with at least one embodiment of the present invention. Importantly, endothelial cells are non-transformed cells. The genetic information of cancer cells is inherently unstable, and tumor cells can mutate and develop resistance to a previously responsive therapeutic modality much faster than a genetically stable population of cells, such as "normal" (i.e., non-cancerous) endothelial cells. Peptide molecules that are able to bind to tumor endothelium specifically could be useful as a delivery vehicle for directing cytotoxic agents to the tumor. Selectively increasing the concentration of a cytotoxic agent within the tumor would affect not only the endothelial cells but also the tumor cells. Mortality due to cancer is the result of uninhibited and metastatic growth of the cancer made possible by the tumor vasculature. Therefore, the ability to destroy tumor vasculature leading to the deterred cancer growth and metastasis would significantly impact the outcome of this disease process. Thus, the present invention will facilitate this directed treatment as an endothelial specific marker that is effective across many vertebrate species.

A number of systems have been developed in recent years that allow for the selection of sequences with desired binding specificities from highly diverse, randomly generated peptide libraries. (For example, see Smith G P, Science 1985; 228:1315; Scott J K, Smith G P, Science 1990; 249:386; and Clackson T, Wells J A, Trends Biotechnol 1994; 12:173.) In these systems, peptides are usually part of a larger fusion protein. Interaction between the peptide and its target molecule may be weakened due to many degrees of conformational freedom as well as the peptide being "hidden" by the fusion protein. To overcome the above limitations, the FliTrx™ E. coli peptide display library (available from Invitrogen, Carlsbad, Calif.), a system incorporating the E. coli thioredoxin, is contemplated for the present invention. This system is shown in the illustration of FIG. 1.

Figure 1:
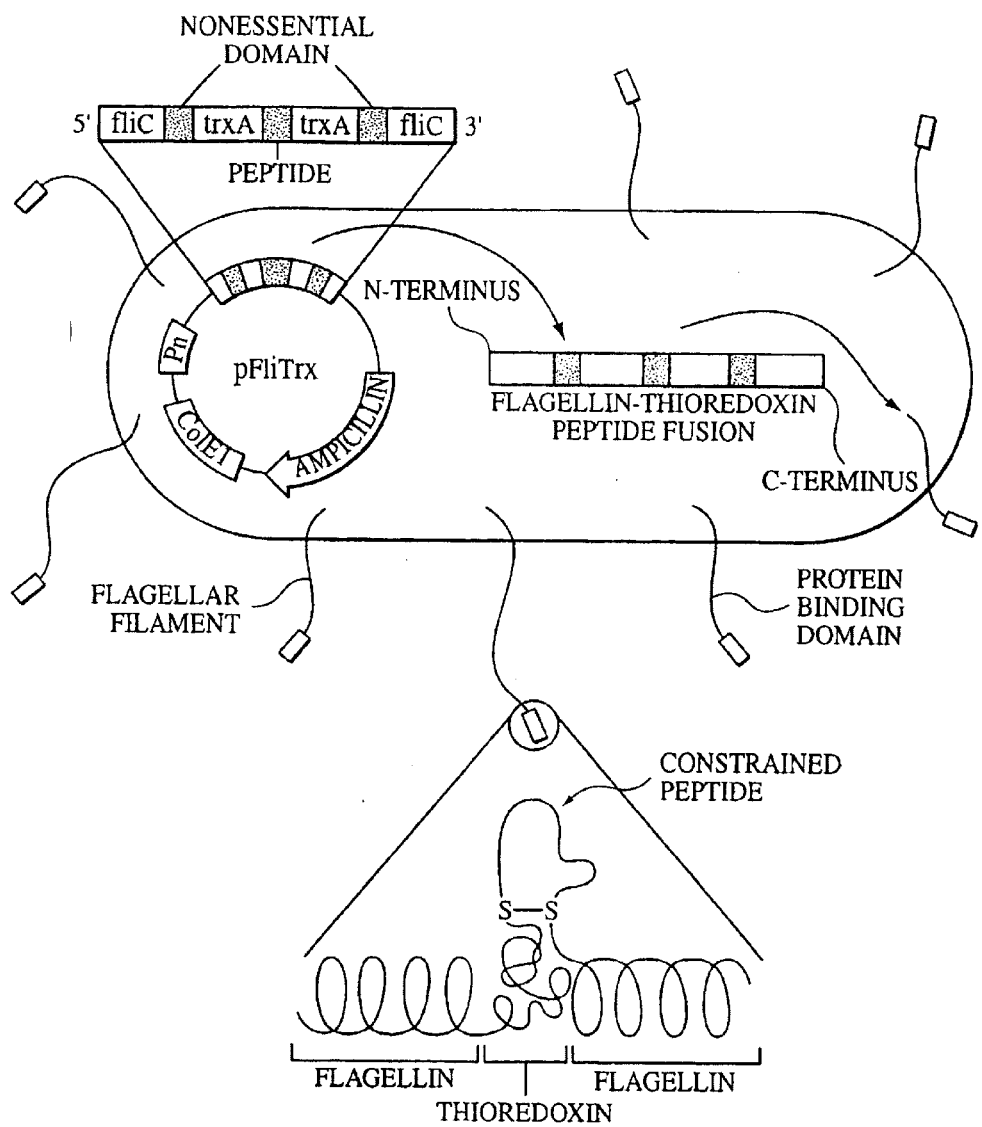
FIG. 1: A diagram illustrating the steps for construction of the peptide Display system of FliTrx™.

As shown in FIG. 1, thioredoxin has a structurally rigid active site formed by the sequence SEQ ID NO 6 -Cys32Gly33Pro34Cys35-. This sequence also forms a tight disulfide loop from the flanking cysteine residues and can accommodate a wide variety of short peptide insertions. The result is that the inserted peptide is presented in a constrained and exposed fashion that maximizes the binding to its target molecule.

Using this method, a 12 amino acid random peptide library constructed within the thioredoxin active site loop was utilized successfully in conjunction with a yeast "interaction-trap" to yield peptides with affinity to human Cdk2 according to Colas P. et al., in Nature 1996; 380:548. By inserting the entire thioredoxin gene into and replacing a central, nonessential portion of the E. coli flagellin gene, a chimeric protein (FliTrx™) was synthesized and exported to the cell surface of the E. coli. As a result, a peptide inserted within the active site of the FliTrx™ thioredoxin would reside on the external surface of the bacterium, maximizing its presentation to the external environment. Using this methodology, a dodecapeptide library within the FliTrx™ thioredoxin active site was used successfully for selecting individual peptides with affinities for immobilized antibody targets.

One aspect of the present invention involves the identification of novel markers on the endothelium specific for the tumor-endothelial cell association. The present invention preferably involves panning the FliTrx™ peptide display library against a monolayer of Matrigel infiltrating cells (MAGIC) in order to remove potential clones binding to angiogenic markers. MAGICs are angiogenic endothelial cells, which infiltrate a subcutaneous fibronectin growth factor and heparin containing Matrigel® deposit (see Baatout S, Anticancer Res 1997; 17:451 and Ito Y et al., Int J Cancer 1996; 67:148, both of which are incorporated herein in their entirety by reference thereto). These cells lack tumor cell interaction and presumably should display only angiogenic markers. In contrast, tumor-derived endothelial cells (TDEC) are endothelial cells from a subcutaneous tumor. The non-binding clones were incubated with TDECs after "subtractive-panning" with MAGIC. The general panning protocol is shown and described in FIG. 2.

This leads to another aspect of at least one embodiment the present invention which is tumor-derived endothelial cells (TDEC) and Matrigel infiltrating cells (MAGIC), and the use of these techniques and cell populations together to substantially subtract out information not specifically related to endothelial cells.

Figure 2:
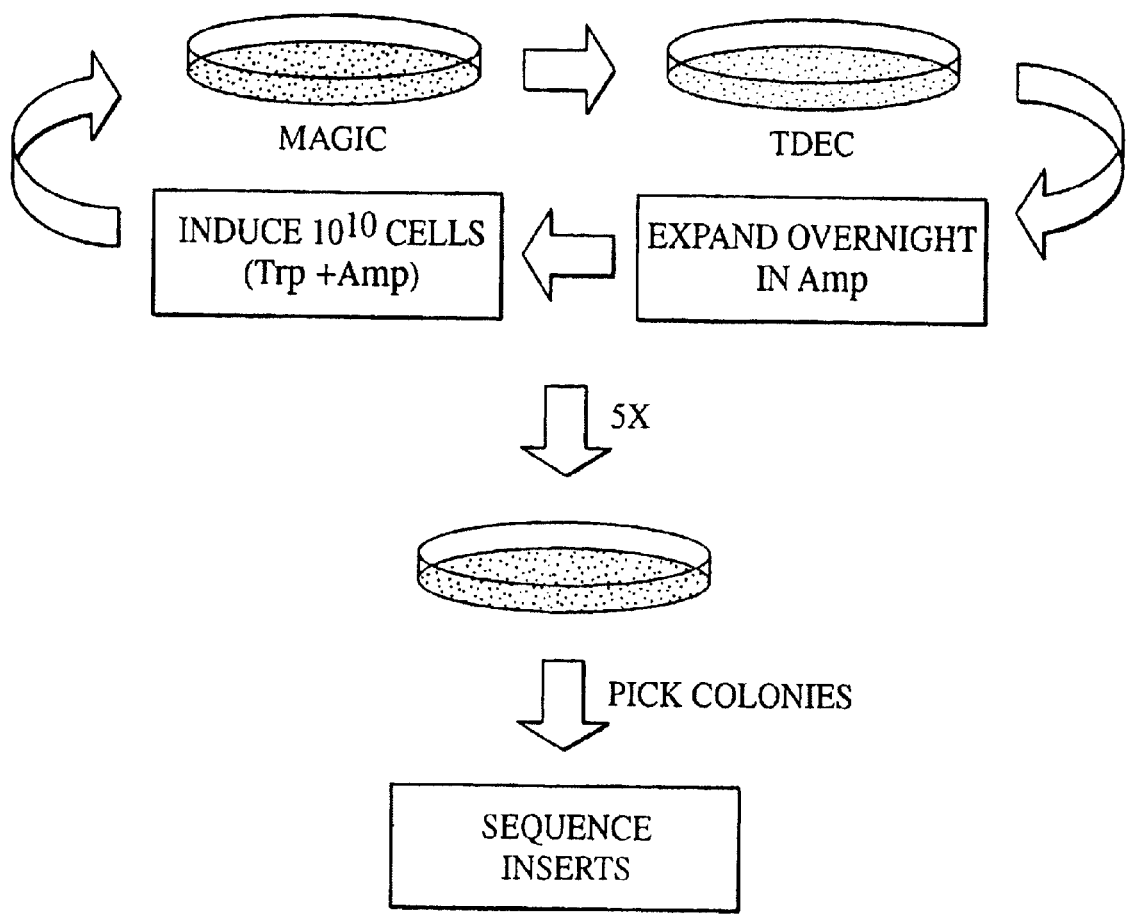
FIG. 2. A diagram illustrating the general panning protocol.

Clones binding to TDECs were then propagated, thus amplifying those clones displaying peptides with binding specificity to tumor endothelial cells. This process was repeated five times, each time removing clones binding to MAGIC while enriching for those binding to TDEC. The results are shown in FIG. 2. Accordingly, an alternative embodiment of the present invention involves "subtractive panning," more specifically, "subtractive panning of TDEC minus MAGIC."

Specifically, one vial of FliTrx™ Peptide Library was used to inoculate 50 ml of IMC medium [1×M9 Salts (40 mM $Na_2HPO_4$, 20 mM $KH_2PO_4$, 8.5 mM NaCl, 20 mM $NH_4Cl$, pH 7.4), 0.2% casamino acids, 0.5% glucose, 1 mM $MgCl_2$] containing 100 µg/ml of ampicillin. The inoculated broths were grown overnight with shaking at 25° C. until $OD_{600}$ is approximately 3. From this culture, $10^{10}$ cells were added to 50 ml of IMC medium containing 100 µg/ml each of ampicillin and tryptophan. This was to induce the expression of the peptides by the E. coli cells and was performed at 25° C. with shaking for 6 hrs. After peptide induction, $10^{10}$ bacterial cells were layered on confluent MAGICs in a 60 mm dish. The incubation was performed at 4° C. for 1 hr in the presence of 10% fetal calf serum (FCS) and 1% α-methyl mannoside. The presence of FCS prevented non-specific protein-protein binding, while that of α-methyl mannoside prevented non-specific protein binding via lectin-like interactions. After 1 hour, the non-binding cells were transferred directly onto TDECs and incubated under similar conditions as that with MAGICs. The TDEC monolayer was washed 5 times with IMC medium containing 10% FCS and 1% α-methyl mannoside (wash solution) to remove non-binding cells. Cells bound to TDECs were dislodged by vigorously vortexing the plate containing 0.75 ml of wash solution for 30 seconds. These cells were then amplified, re-induced for peptide expression, and the process of panning was repeated four additional times.

In order to survey for potential peptide sequences which will bind molecular markers specific for tumor-endothelial interaction, inserts encoding for the displayed peptides from 100 randomly picked bacterial clones were sequenced. This was accomplished as follows. Frozen stocks of cells from the fifth panning samples were plated at various dilutions on RMG-Amp agar plates (1×M9 salts, 0.2% casamino acids, 0.5% glucose, 1 mM $MgCl_2$, 100µg/ml ampicillin) at 30° C. overnight. One hundred individual colonies were picked the following day and were used to inoculate 3 ml of RM medium (1×M9 salts, 2% casamino acids, 1% glycerol, 1 mM $MgCl_2$) containing 100 µg/ml ampicillin. The inocula were incubated with shaking at 30° C. for 16–18 hours until $OD_{600}$ is between 2 and 3. Frozen stocks in 15% glycerol were made from 850 µl suspensions of each clone. The remainder of each culture was used for plasmid DNA purification.

Figure 3A:
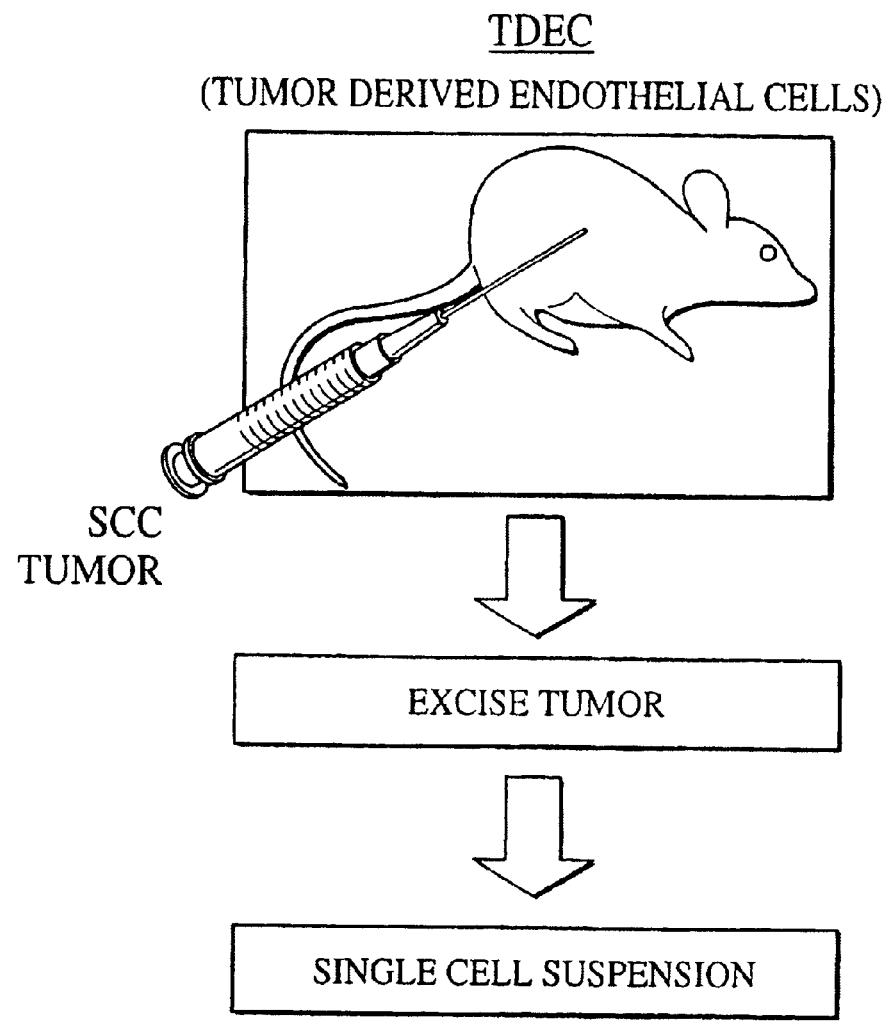
FIG. 3. A schematic illustrating the generation of TDECs (FIG. 3A) and MAGICs (FIG. 3B)

TDECs are endothelial cells isolated from SCC VII murine squamous cell tumors in C3H/HeJ mice as shown in FIG. 3A. Tumors were established by subcutaneous injection of 5×10⁶ SCC VII cells per C3H/HeJ mouse. After a tumor had achieved a diameter of 0.5 cm to 1.0 cm and before any evidence of central necrosis, it was removed sterilely, minced, and digested with collagenases and RNAses to yield a single cell suspension. The cells were then stained using antibody for PECAM-1. The stained cells were sorted using automated flow cytometry and the positive cells were cultured as TDECs in Po Media [DMEM supplemented with 20% Sarcoma-180 conditioned media, 10% Fetal Calf Serum, 1% BME vitamin, 1% heparin, and 0.005% endothelial cell growth supplement (Collaborative Research)].

Figure 3B:
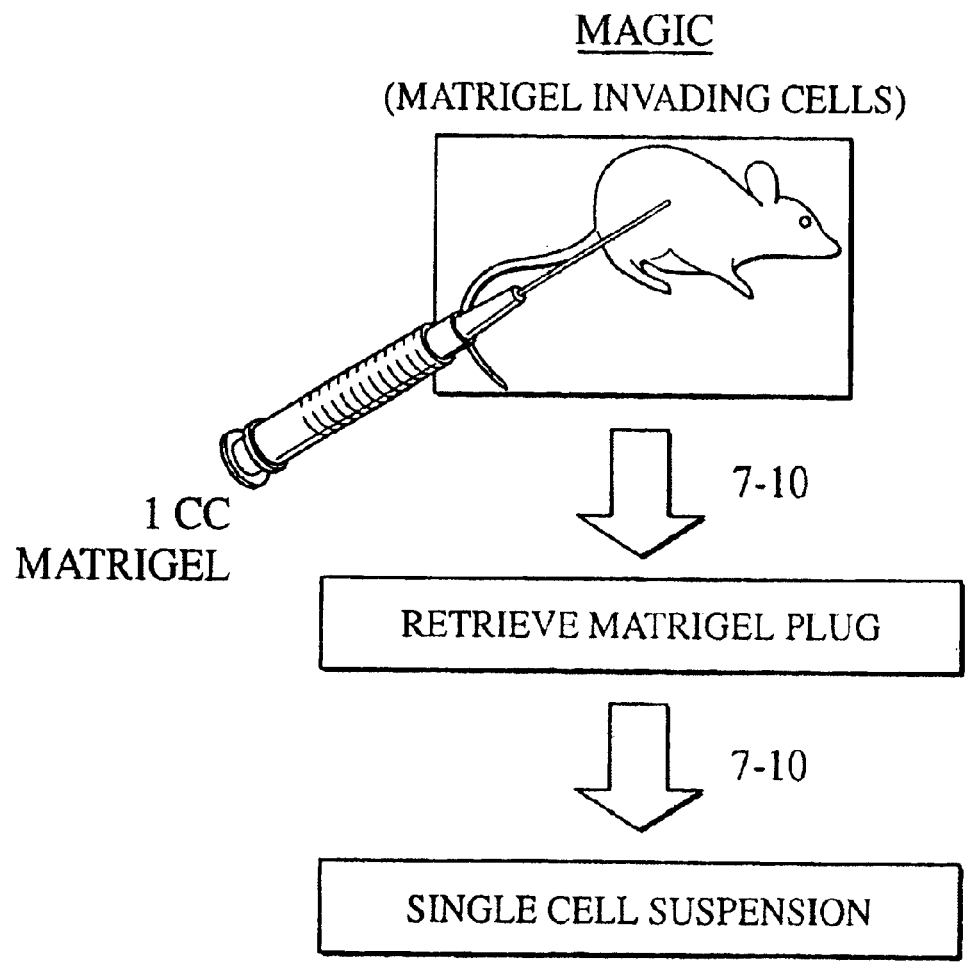

MAGICs were cultured in a similar fashion as shown in FIG. 3B. Approximately 7–10 days after the Matrigel® injection, the plug was removed and cultured in vitro in Po Media for additional 7–10 days. Single cell suspension was prepared by digesting the Matrigel® plug in Dispase®. The cells were then cultured in Po Media.

Evidence for specific binding of oligopeptides to TDEC was accomplished as follows. The most frequently repetitive sequences obtained from the 100 clones were used for synthesis of oligopeptides (Sigma Genesis). By conjugating fluorescein isothiocynate (FITO) to the carboxyl termini of peptides, these molecules were tested for in vitro binding with TDECs and NIH3T3 cells (negative control cell line). These peptides contained flanking cysteines so that a disulfide loop may be reformed, thus constraining and mimicking the binding condition of the initial selection process. Positive and negative control peptides were SEQ ID NO 7 PepRGD ($H_2$N-Cys-Glu-Leu-Arg-Gly-Asp-Gly-Trp-Cys-$CO_2$H) and SEQ ID NO 8 $PepG_7$ ($H_2$N-Cys-$Gly_7$-Cys-$CO_2$H), respectively. The control peptide SEQ ID NO 8 $PepG_7$ is not expected to have any specific binding to membrane proteins, while SEQ ID NO 7 PepRGD has been reported to bind angiogenic endothelial cells, and therefore, should bind both MAGICs and TDECs. In some experiments, poly-L-lysine was also used as a positive control peptide. Monolayers of NIH3T3 and TDECs on glass slide wells were incubated with peptides at 5 µg/ml (1 µg of peptide per 200µ well) overnight at 37° C. in phosphate buffered saline (PBS) with 10%FCS. After washing the cells with PBS with 10%FCS for 3 times at 37° C./15 minutes, fluorescent microscopy of the cells was performed.

Following panning of the FliTrx library against MAGIC and TDEC, one hundred colonies were picked randomly for sequencing of the inserts. The resulting sequencing data were then analyzed for repeats. Those repeated sequences (3-mer or greater) are listed in FIG. 4. There were a total of 17 repeat sequences isolated-thirteen 3-mers and four 4-mers.

An important conclusion of the peptide analysis revealed a distinct charge motif. The individual amino acids were scored as positively charged (+), negatively charged (-), neutral and hydrophilic Ø, or neutral and hydrophobic (O) at physiologic conditions. This analysis revealed that of all the repeats, seventeen 3-mer clones (34% of analyzed clones, and twenty-three 3- or 4-mer clones or 46% of analyzed clones) depicted the positive-positive-hydrophobic motif (++O) as shown in Table 2.

Combining the data from FIG. 4 and Table 2, five peptide sequences were identified to be tested for binding specificity to TDEC. These five peptide sequences are shown in Table 3 with the targeting residues illustrated by three-letter designations. The test peptides are labeled SEQ ID NO 1–5. The control peptide SEQ ID NO 8 Pep $G_7$ consists of seven glycine residues flanked by cysteines. This peptide should have no binding specificity to TDEC and serves as the negative control peptide. SEQ ID NO 7 PepRGD has reported specificity for tumor endothelium and serves as the positive control peptide.

TABLE 2

Frequency of Peptide Repeats Based on the Chemical Properties of the Amino Acids.

| | |
|---|---|
| ++O | 17 |
| ++Ø | 9 |
| Ø++ | 8 |
| +Ø+ | 5 |
| Ø++Ø | 3 |
| Ø++O | 2 |
| O++O | 2 |
| ++OO | 2 |
| O++ | 2 |
| +++ | 2 |
| Ø+Ø | 2 |
| Ø+O | 2 |
| +ØO | 2 |

TABLE 3

Sequences of Test Peptides

Seq ID No 1 Cys-Gly-Gly-Arg-His-Ser-Gly-Gly-Cys

Seq ID No 2 Cys-Gly-Gly-Arg-Lys-Leu-Gly-Gly-Cys

Seq ID No 3 Cys-Gly-Gly-Arg-Arg-Leu-Gly-Gly-Cys

Seq ID No 4 Cys-Gly-Gly-Arg-Arg-Ser-Arg-Gly-Gly-Cys

Seq ID No 5 Cys-Leu-Leu-Arg-Arg-Ser-Arg-Leu-Leu-Cys

Seq ID No 8 $PepG_7$ Cys-Gly-Gly-Gly-Gly-Gly-Gly-Gly-Cys

Seq ID No 7 PepRGD Cys-Glu-Leu-Arg-Gly-Asp-Gly-Trp-Cys

Figure 5:
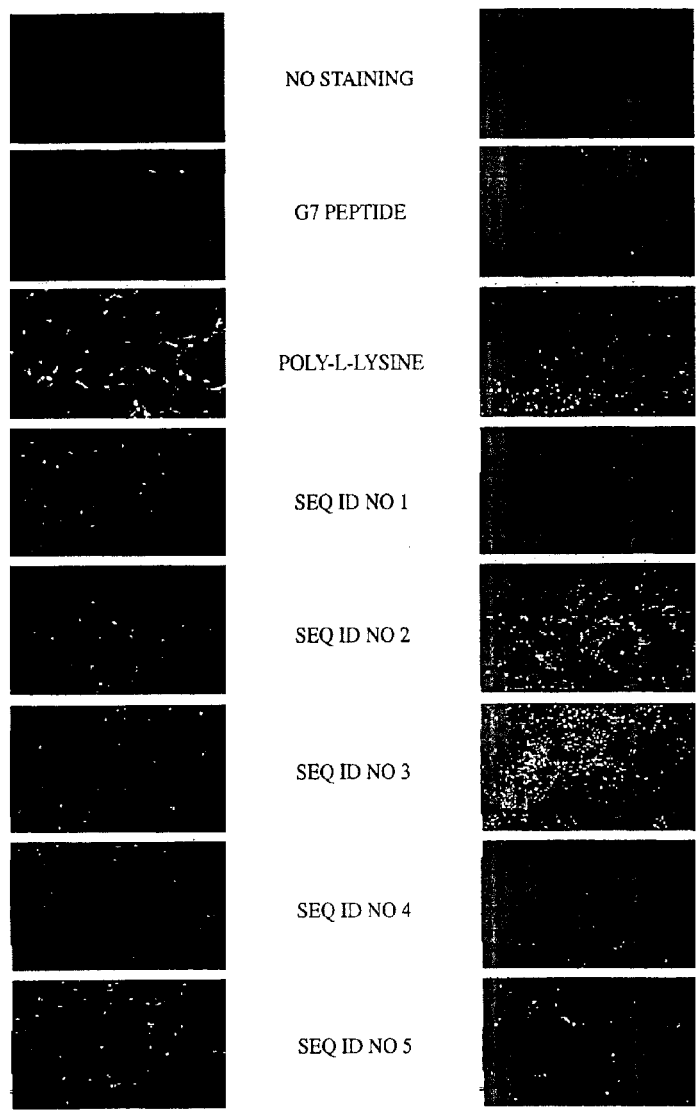
FIG. 5. Micrographs showing the in vitro binding of FITC-conjugated targeting peptides SEQ ID NO 1–5 to TDEC and NIH 3T3.
Figure 6:
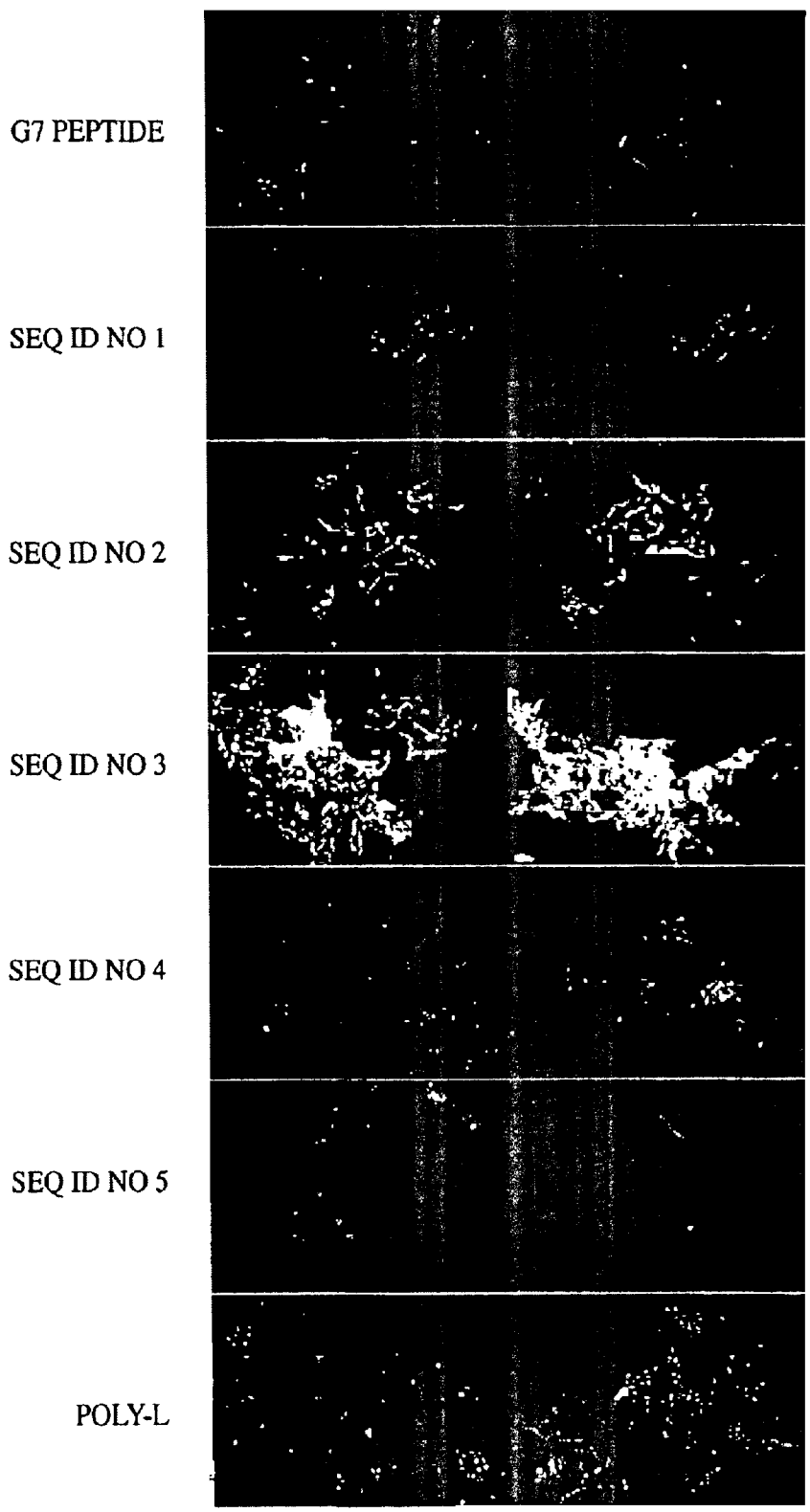
FIG. 6. Micrographs showing in vitro binding of FITC conjugated targeting peptides SEQ ID NO 1–5 with TDEC.

In order to determine the endothelial specificity of the SEQ ID NO 1–5 peptides, in vitro binding experiments with TDEC monolayers were performed. In these experiments, NIH3T3 was used as the negative control monolayer. The results of this binding experiment are depicted in FIGS. 5 and 6. As shown in both FIGS. 5 and 6, labeled SEQ ID NO 3 containing the targeting residues Arg-Arg-Leu consistently showed the brightest staining and specificity for TDEC. SEQ ID NO 2 with the targeting residues Arg-Lys-Leu also showed preferential staining for TDEC, however, binding of FITC labeled SEQ ID NO 2 to TDEC did not yield as high a level as did binding of SEQ ID NO 3 to TDEC. The targeting motifs of SEQ ID NO 3 and SEQ ID NO 2 both conform to the positive-positive-hydrophobic (++O) motif.

Additionally, in vivo experiments with the prototype peptide, SEQ ID NO 3, which stained the brightest in the in vitro experiments described above, were conducted using several different assays as described below. In one in vivo assay, tumor-bearing mice were injected five times intravenously (tail vein) with 1 ng/mouse at one hour intervals. The mice were sacrificed 15 minutes after the final injection, the tumors and other normal tissues (lung, heart, muscle) were taken for fresh frozen sectioning (i.e., embedded in OCT medium and frozen) and for evaluation via fluorescence microscopy. The assay showed a preferential binding of SEQ ID NO 3 for the vessels in the tumors, with no binding to the vessels of normal tissues. This result has been observed in murine SCC (squamous cell) as well as in human xenograft PC-3 (prostate carcinoma) tumor models. These results illustrate the wide cross-reactivity of these peptides, especially that of SEQ ID NO 3. Although these peptides were generated from TDEC originating from the murine SCC tumor, SEQ ID NO 3 also bound to the endothelium from a human xenograft model.

Figure 7A:
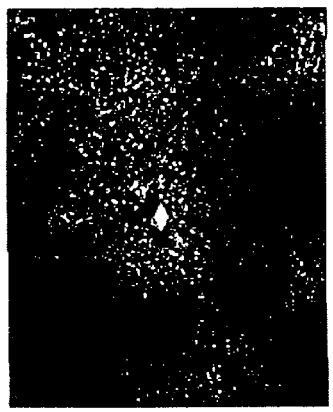
FIG. 7. Micrographs showing in vivo binding of targeting peptides SEQ ID NO 1–5 to mouse PC-3 tumor sections.
Figure 7B:
Figure 7C:
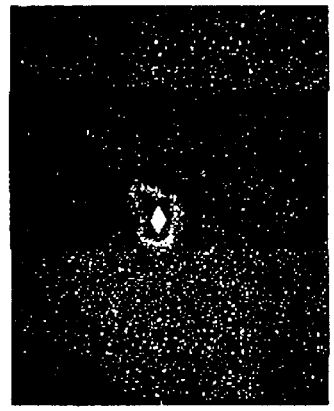

The specificity of SEQ ID NO 3 for endothelial vessels is illustrated in FIG. 7. In this experiment, PC-3 tumor-bearing mice were injected (as described above) with positive control poly-L-lysine, negative control SEQ ID NO 8 Pen $G_7$ and peptide SEQ ID NO 3. FIG. 7A, 7B and 7C are micrographs illustrating cross-sections of PC-3 tumor from tumor-bearing mice that were injected with peptides. In each figure, the gray diamond indicates the location of the lumen of the blood vessel. FIG. 7A is poly-L-lysine injection that is not only bound to the cells of the blood vessel, but also diffused through the intercellular space. FIG. 7B is the negative control injection, SEQ ID NO 8 Pep $G_7$, which showed no binding activity. FIG. 7C displays the distribution of SEQ ID NO 3 binding following injection. An intense binding to the cells of the vessel observed. However, staining was limited to the blood vessel wall, i.e. endothelial cells.

Figure 8:
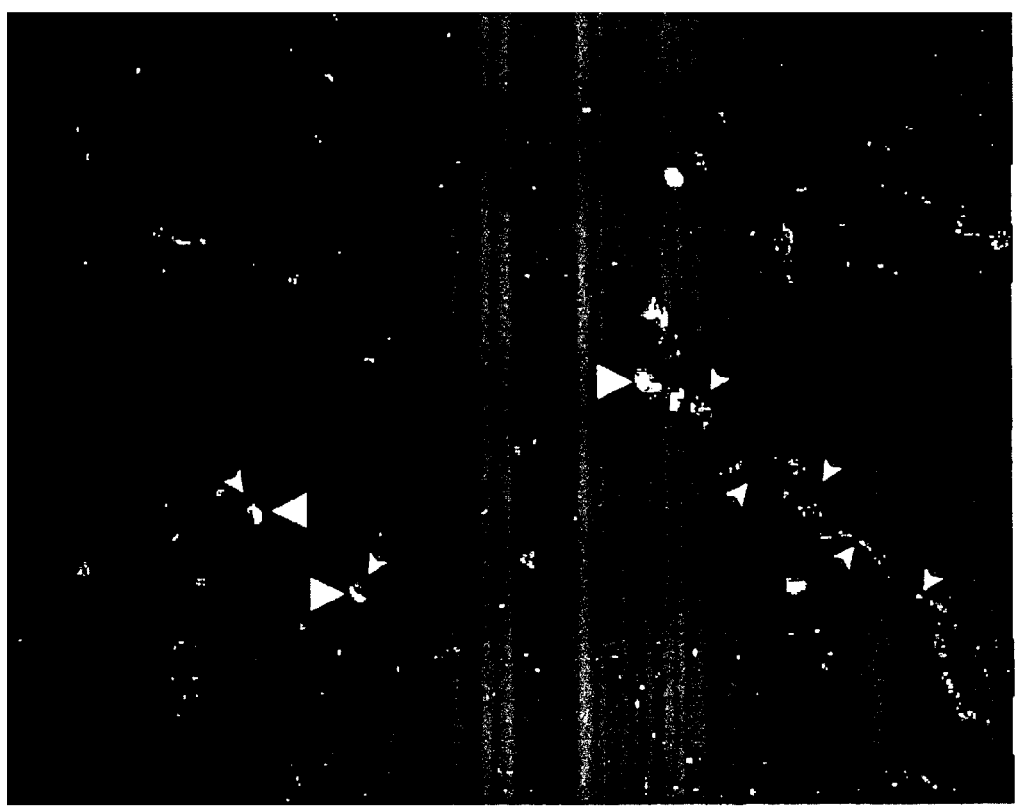
FIG. 8. Micrographs showing in vivo binding of targeting peptide SEQ ID NO 3 to vascularized regions of human sarcoma.

The ability of novel peptide motifs of the present invention to cross-react with tissues from different sources was tested using human samples from a pathologist-diagnosed soft tissue sarcoma and a prostate carcinoma. Fresh frozen tumor sections were snap fixed in paraformaldehyde, and then triple stained for fluorescence microscopic analysis, the results of which are shown in FIG. 8. The staining included: a stain for cell nuclei, and anti-Factor VIII antibody (secondary antibody labeled with Cy3 red fluorescent probe), and peptide SEQ ID NO 3 (tagged with FITC, green upon fluorescence). Analysis revealed even, ubiquitous staining for cell nuclei indicating cell-dense tissue sections. Factor VIII staining (marked with smaller arrowheads) demonstrated that the tumor sections were vascularized and that there were vessel-like areas, some in cross-section, but many in longitudinal section. Factor VIII staining is specific for endothelial cells which produce and store the Factor VIII blood factor. Staining for SEQ ID NO 3 (marked with large arrowheads) was observed primarily in the regions of the tissue that were vascularized as indicated by staining with Factor VIII. These data show that ++O motif peptide sequences, with SEQ ID NO 3 as the model, are specific for the endothelium of tumors, and importantly that the motif specificity is not limited to a particular species.

These peptides are likely to have significant applications in human cancer therapeutics. Peptide molecules that are able to bind to tumor endothelium specifically could be used as a delivery vehicle for carrying cytotoxic agents to the tumor. Importantly, the novel peptides of the present invention are small, preferably less than 50 amino acid residues in length, and therefore are unlikely to elicit unwanted immune responses in the host. The selective increased concentration of the cytotoxic agent within the tumor would affect not only the endothelial cells but also the tumor cells. Mortality due to cancer is the result of uninhibited and metastatic growth of the cancer made possible by the tumor vasculature. Therefore, the ability to destroy tumor vasculature leading to deterred cancer growth and metastasis would impact significantly on the natural outcome of this disease process.

Aside from therapeutic targeting of the tumor vasculature, targeting peptides of the present invention that specifically bind to tumor endothelium can be used as a possible diagnostic tool. The small size of the peptides of the present invention are also desirable for these diagnostic purposes. For example, patients can present with occult tumors, or with nonspecific radiologic findings. Potentially, these targeting peptide molecules can be conjugated to radiologically 'visible' molecules and used to enhance imaging studies (e.g., magnetic resonance imaging scans, positron emission tomography, and computed axial tomography) in such patients, thus permitting the localization and diagnosis of these tumors. Additionally, by using the peptides, molecular targets that are bound by the peptides can be isolated and identified. These molecular targets can then be used as potential tumor specific antigens for tumor immunotherapeutics. Furthermore, these molecular targets can also be used as potential tumor markers in patients' sera for the molecular detection of cancer cells. Thus, the identification of peptide motifs, which will bind specifically to tumor endothelium, has many therapeutic and diagnostic implications.

From the in vitro panning experiments it has been determined that the recurring targeting peptide sequences are 3-mer (13 sequences) and 4-mer (4 sequences). The majority of the detected sequences are basic and arginine is the most common amino acid. The most frequent chemical arrangement of the repeated peptides conforms to the positive-positive-hydrophobic (++O) motif. Peptide SEQ ID NO 3 (with the targeting residues Arg-Arg-Leu) appears to have the highest in vitro binding specificity to TDEC while Peptide SEQ ID NO 2 (with targeting residues Arg-Lys-Leu) also exhibits some binding specificity to TDEC. Both SEQ ID NO 3 and SEQ ID NO 2 conform to the (++O) motif. Accordingly, a preferential part of the present invention is a peptide sequence or fragment that is less than 50 amino acid residues in length and includes a 3-mer or a 4-mer, preferably including an arginine amino acid, basic amino acids, even more preferably. It is most preferable to have a peptide sequence which includes a positive-positive-hydrophobic motif.

The agent that is linked to the targeting peptide will, of course, depend on the ultimate application of the invention. Where the aim is to provide an image of the tumor, one will desire to use a diagnostic agent that is detectable upon imaging, such as a paramagnetic, radioactive or fluorogenic agent as described and disclosed in U.S. Pat. 6,051,230 which is incorporated by reference herein in its entirety. Many diagnostic agents are known in the art to be useful for imaging purposes, as are methods for their attachment to antibodies (see, e.g., U.S. Pat. Nos. 5,021,236 and 4,472,509, both incorporated herein by reference). In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and erbium (III), with gadolinium being particularly preferred. Ions useful in other contexts, such as X-ray imaging, include but are not limited to lanthanum (III), gold (III), lead (II), and especially bismuth (III). Moreover, in the case of radioactive isotopes for therapeutic and/or diagnostic application, one might mention iodine$^{131}$, iodine$^{123}$, technicium$^{99}$, indium$^{111}$, rhenium$^{188}$, rhenium$^{186}$, gallium$^{67}$, copper$^{67}$, yttrium$^{90}$, iodine$^{125}$ or astatine$^{211}$.

For certain applications, it is envisioned that the therapeutic agents will be pharmacologic agents will serve as useful agents for attachment to antibodies or growth factors, particularly cytotoxic or otherwise anticellular agents having the ability to kill or suppress the growth or cell division of endothelial cells. In general, the invention contemplates the use of any pharmacologic agent that can be conjugated to a targeting peptide and delivered in active form to the targeted tumor endothelium. Exemplary anticellular agents include chemotherapeutic agents, radioisotopes as well as cytotoxins. In the case of chemotherapeutic agents, the inventors propose that agents such as a hormone such as a steroid; an antimetabolite such as cytosine arabinoside, fluorouracil, methotrexate or aminopterin; an anthracycline; mitomycin C; a vinca alkaloid; demecolcine; etoposide; mithramycin; or an antitumor alkylating agent such as chlorambucil or melphalan, will be particularly preferred. Other embodiments may include agents such as a coagulant, a cytokine, growth factor, bacterial endotoxin or the lipid A moiety of bacterial endotoxin. In any event, it is proposed that agents such as these may, if desired, be successfully conjugated to a targeting agent, preferably an antibody, in a manner that will allow their targeting, internalization, release or presentation to blood components at the site of the targeted endothelial cells as required using known conjugation technology (see, e.g., Ghose et al., 1983 and Ghose et al., 1987).

In certain preferred embodiments, therapeutic agents will include generally a plant-, fungus- or bacteria-derived toxin, such as an A chain toxins, a ribosome inactivating protein, .alpha.-sarcin, aspergillin, restrictocin, a ribonuclease, diphtheria toxin or pseudomonas exotoxin, to mention just a few examples. The use of toxin-antibody constructs is well known in the art of immunotoxins, as is their attachment to antibodies. Of these, a particularly preferred toxin for attachment to antibodies will be a deglycosylated ricin A chain. Deglycosylated ricin A chain is preferred because of its extreme potency, longer half-life, and because it is economically feasible to manufacture it a clinical grade and scale.

Details on techniques for formulation and administration of pharmaceuticals may be found in the latest edition of *Remington's Pharmaceutical Sciences* (Mack Publishing Co., Easton, Pa.).

As recapitulated herein, embodiments of the invention correspond to specific novel peptide sequences which define specificity of tumor-derived endothelial cells (TDEC). The physical characteristic of charge conformation of these motifs is important, specifically, peptides containing the charge motif of positive-positive-hydrophobic. Identification of novel peptides and their corresponding charge motifs will be useful in diverse diagnostic tests and therapeutic treatments.

Although the preferred methods have been described in detail, it should be understood that various changes, substitutions, and alterations can be made in the present invention without deviating from the concepts provided herein. For example, the preferred peptide sequences can be included in synthetic proteins as well as a variety of therapeutic formulations.

REFERENCES

The following references are incorporated herein by reference in their entirety; for a more detailed understanding of the field of the invention: Pierschbacher M D, Ruoslahti E. The cell attachment activity of fibronectin can be duplicated by small fragments of the molecule. Nature 1984; 309:30; Koivunen E, Gay D, Ruoslahti E. Selection of peptides binding to the $\alpha_5\beta_1$ integrin from phage display library. J Biol Chem 1993; 268: 20205; Koivunen E, Wang B, Ruoslahti E. Isolation of a highly specific ligand for the $\alpha_5\beta_1$ integrin from a phage display library. J Cell Biol 1994; 124:373; Healy J M, Murayama O, Maeda T, et al. Peptide ligands for integrin $\alpha_5\beta_3$ selected from random phage display libraries. Biochemistry 1995; 34:3948; Pasqualini R, Ruoslahti, E. Organ targeting in vivo using phage display peptide libraries. Nature 1996; 380:364; Rajotte D, Arap W, Hagedorn M, et al. Molecular heterogeneity of the vascular endothelium revealed by in vivo phage display. J Clin Invest 1998; 102:430; Pasqualini R, Koivunen E, Kain R. et al. Aminopeptidase N is a receptor for tumor-homing peptides and a target for inhibiting angiogenesis. Ca Res 2000; 60:722; Smith G P. Filamentous fusion phage: novel expression vectors that display cloned antigens on the virion surface. Science 1985; 228:1315; Scott J K, Smith G P. Searching for peptide ligands with an epitope library. Science 1990; 249:386; Clackson T, Wells J A. In vitro selection from protein and peptide libraries. Trends Biothechnol 1994; 12:173; Colas P, Cohen B, Jessen T, et al. Genetic selection of peptide aptamers that recognize and inhibit cyclin-dependent kinase 2. Nature 1996; 380:548; Lu Z, Murray K S, van Cleave V, et al. Expression of thioredoxin random peptide libraries on *Escherichia coli* (*E. coli*) cell surface as functional fusions to flagellin: a system designed for exploring protein-protein interactions. Bio/Technology 1995; 13:366; Baatout S. Endothelial differentiation using Matrigel (Review). Anticancer Res 1997; 17:451;

The following references are incorporated herein in their entirety by reference for background purposes: Zhu D, Pauli B U. Generation of monoclonal antibodies directed against organ-specific endothelial cell surface determinants. J Histochem Cytochem 1991; 39:1137; Pierschbacher M D, Ruoslahti E. Variants of the cell recognition site of fibronectin that retain attachment-promoting activity. Proc Natl Acad Sci USA 1984; 81:5985; Yamada K M, Kennedy D W. Dualistic nature of adhesive protein function: fibronectin and its biologically active peptide fragments can autoinhibit fibronectin function. J Cell Biol 1984; 99:29; Gartner T K, Bennett J S. The tetrapeptide analog of the cell attachment site of fibronectin inhibits platelet aggregation and fibrinogen binding to activated platelets. J Biol Chem 1985; 260:11891; Plow E F, Pierschbacher M D, Ruoslahti E, et al. The effect of Arg-Gly-Asp containing peptides on fibrinogen and von Willebrand factor binding to platelets. Proc Natl Acad Sci USA 1985; 82:8057; Suzuki S, Oldberg A, Hayman E G, et al. Complete amino acid sequence of human vitronectin deduced from cDNA. Similarity of cell attachment sites in vitronectin and fibronectin. EMBO J 1985; 4:2519; Gardner J M, Hynes R O. Interaction of fibronectin with its receptor on platelets. Cell 1985; 42:439; Ito Y, Iwamoto Y, Tanaka K, et al. A quantitative assay using basement membrane extracts to study tumor angiogenesis in vivo. Int J Cancer 1996; 67:148.

The following references are incorporated herein by reference in their entirety for experimental techniques which are known and relate to aspects of the invention: Pasqualini R. Koivunen E, Kain R, et al. Aminopeptidase N is a receptor for tumor-homing peptides and a target for inhibiting angiogenesis. Ca Res 2000; 60:722; Scott J K, Smith G P. Searching for peptide ligands with an epitope library. Science 1990; 249:386; Lu Z, Murray K S, van Cleave V, et al. Expression of thioredoxin random peptide libraries on *Escherichia coli* cell surface as functional fusions to flagellin: a system designed for exploring protein-protein interactions. Bio/Technology 1995; 13:366; Modzelewski R A, Davies P, Watkins S C, Auerback R, Chang M-J, Johnson C S. Isolation and identification of fresh tumor-derived endothelial cells from a murine RIF-1 fibrosarcoma. Ca Res 1994, 54:336–339.

What is claimed is:

1. A composition useful for targeting tumor-derived endothelial cells, said composition comprising a peptide selected from the group consisting of SEQ ID NO 1 Cys-Gly-Gly-Arg-His-Ser-Gly-Gly-Cys; SEQ ID NO 2 Cys-Gly-Gly-Arg-Lys-Leu-Gly-Gly-Cys; SEQ ID NO 3 Cys-Gly-Gly-Arg-Arg-Leu-Gly-Gly-Cys; SEQ ID NO 4 Cys-Gly-Gy-Arg-Arg-Ser-Arg-Gly-Gly-Cys; and SEQ ID NO 5 Cys-Leu-Leu-Arg-Arg-Ser-Arg-Leu-Leu-Cys.

2. The composition of claim 1, wherein said peptide is operatively attached to a therapeutic agent that is capable of exerting a cytotoxic effect on tumor vasculature.

3. The composition of claim 1, wherein said peptide is operatively attached to a therapeutic agent capable of exerting a cytotoxic effect on a tumor.

4. The composition of claim 2 or 3, wherein the therapeutic agent includes at least one agent selected from the group consisting essentially of anticellular agents, chemotherapeutic agents, radioisotopes, and cytotoxins.

5. The composition of claim 4, wherein the therapeutic agent is an anticellular agent and said anticellular agent comprises a steroid, an antimetabolite, an anthracycline, a vinca alkaloid, an antibiotic, an alkylating agent, or an epipodophyllotoxin.

6. The composition of claim 4, wherein the therapeutic agent is an anticellular agent and said anticellular agent comprises a plant-, fungus-or bacteria-derived toxin.

7. The composition of claim 4, wherein said therapeutic agent is a cytotoxin and said cytotoxin comprises an A chain toxin, a ribosome inactivating protein, gelonin, alpha-sarcin, aspergillin, restrictocin, a ribonuclease, diphtheria toxin, *Pseudomonas* exotoxin, a bacterial endotoxin, or the lipid A moiety of a bacterial endotoxin.

8. The composition of claim 1, formulated as a pharmaceutical composition.

9. The composition of claim 2, wherein the peptide attached to a therapeutic agent is capable of exerting a cytotoxic effect on tumor vasculature sufficient to lead to tumor necrosis.

10. The composition of claim 1, wherein said peptide is linked to a diagnostic agent that is detectable upon imaging.

11. The composition of claim 10, wherein said diagnostic agent is selected from the group consisting of paramagnetic ions, radioactive ions and fluorogenic ions detectable upon imaging.

12. The composition of claim 11, wherein said diagnostic agent is a paramagnetic ion, and said paramagnetic ion is selected from the group consisting essentially of chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and erbium (III).

13. The composition of claim 11, wherein said diagnostic agent is a radioactive ion, and said radioactive ion is selected from the group consisting essentially of iodine$^{123}$, technetium$^{99m}$, rhenium$^{188}$, rheniumi$^{186}$, copper$^{67}$, iodine$^{131}$, yttrium$^{90}$, iodine$^{125}$, astatine$^{211}$, and gallium$^{67}$.

* * * * *

UNITED STATES PATENT AND TRADEMARK OFFICE
CERTIFICATE OF CORRECTION

PATENT NO. : 6,974,791 B2  Page 1 of 1
APPLICATION NO. : 09/810700
DATED : December 13, 2005
INVENTOR(S) : Michael K. Wong et al.

It is certified that error appears in the above-identified patent and that said Letters Patent is hereby corrected as shown below:

Column 6, line 67: delete "FITO" and insert therefor --FITC--.

Column 7, line 17: delete "µ and insert therefor --µl--.

Column 7, line 44: delete "Pep $G_7$" and insert therefor --Pep$G_7$--.

Column 8, line 54: delete "Pen $G_7$" and insert therefor --Pep$G_7$--.

Column 8, line 62: delete Pep $G_7$" and insert therefor --Pep$G_7$--.

Claim 7, line 3: delete "alpha-sarcin" and insert therefor --.alpha.-sarcin--.

Claim 13, line 4: "technetium$^{99m}$", add --indium$^{111}$--.

Claim 13, line 4: delete "rheniumi$^{186}$" and insert therefor --rhenium$^{186}$--.

Signed and Sealed this

Twelfth Day of December, 2006

JON W. DUDAS
*Director of the United States Patent and Trademark Office*